July 14, 1964 F. W. ANDERSON Plant Pat. 2,426
ALMOND TREE
Filed May 27, 1963
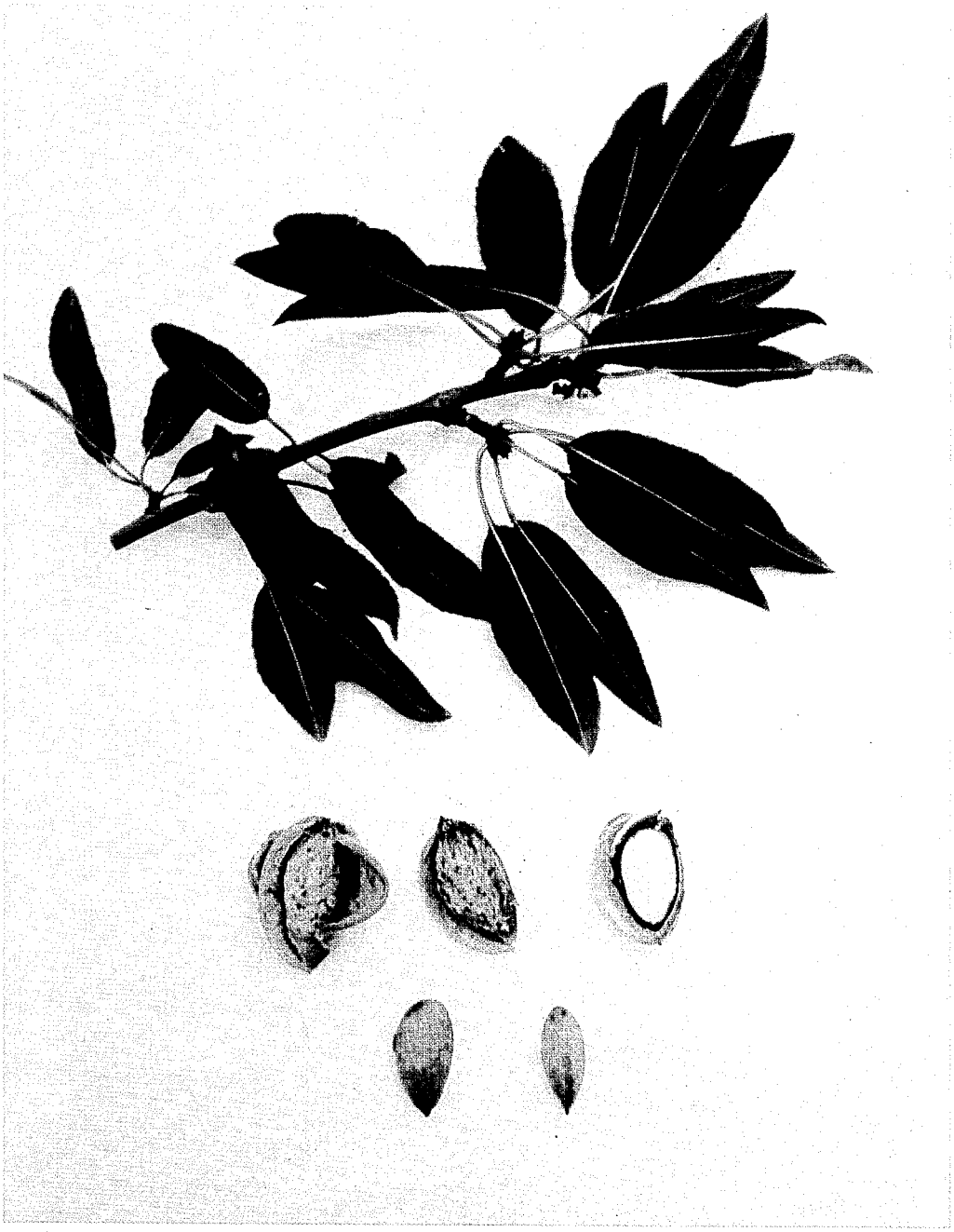
INVENTOR
*Frederic W. Anderson*
*Webster & Webster*
ATTYS.

United States Patent Office

Plant Pat. 2,426
Patented July 14, 1964

2,426
ALMOND TREE

Frederic W. Anderson, Merced, Calif., assignor to Fowler Nurseries, Inc., Newcastle, Calif., a corporation of California Filed May 27, 1963, Ser. No. 283,637
1 Claim. (Cl. Plt.—30)

This discovery relates to a new and distinct variety of almond tree which bears general resemblance, both in tree and nuts, to the Nonpareil (unpatented) which has long been the most important commercial variety in California; the present variety being an improvement over the Nonpareil by virtue of the following novel and characteristic features:

The tree is larger, as well as more vigorous and upright in growth.

The period of full bloom, in point of time, is about halfway between the Nonpareil and Mission (unpatented); being approximately three or four days after the former and two or three days before the latter. The present variety is, however, intercompatible with the Nonpareil and Mission, and—blooming between such varieties—overlaps enough to pollenize and set good crops on both.

The crop production is greater but with nuts and kernels which, while closely resemblnig the Nonpareil, are on the average ten to twenty percent smaller. Consequently, there is a larger percentage, in the crop, of the smaller sizes of kernels as required for use in confections.

The present variety of almond tree was discovered by me as a sprout growing from below the graft union of a Nonpareil tree in my orchard located near Le Grand, in the county of Merced, California.

Subsequent to its discovery, and upon recognition by me of its novel and distinctive characteristics, I asexually reproduced the variety, in my orchard located as aforesaid, by top-working on mature orchard trees. Such asexual reproductions, in maturity, were found to run true to the parent in all respects.

The drawing comprises an illustration, by photographic reproduction in color, of a first year shoot with leaves; a nut with the hull thereon but open; a nut with the hull removed; a nut with half the shell removed and the kernel cut to expose the meat; a kernel from one side; and another kernel from one edge.

Referring now more specifically to the botanical details of this new and distinct variety of almond tree, the following is an outline description thereof; all major color plate identifications, by comparison with fresh specimens, being by reference to Maerz and Paul Dictionary of Color; except where common terms of color definition are employed:

Tree:
- *Density.*—Open.
- *Size.*—Large.
- *Vigor.*—Vigorous.
- *Branching hibit.*—Upright.

Foliage: Quantity—abundant.

Leaves:
- *Size.*—Average length—4 1/16". Average width—15/16".
- *Shape.*—Ovate.
- *Margin.*—Crenate.
- *Color.*—At approximately time of harvest—Medium Green (23–J–5).

Bloom:
- *Amount of bloom.*—Heavy.
- *Color.*—White.
- *Blooming period.*—About halfway between Nonpareil and Mission; being approximately three or four days after the former and two or three days before the latter.

Crop:
- *Bearing.*—Regular bearer.
- *Productivity.*—Heavy to very heavy.
- *Distribution of nuts on tree.*—Well distributed.
- *Harvest period.*—Very early, about with Nonpareil.
- *Tenacity.*—Hangs well on tree; easy to harvest; easy to hull.

Hull:
- *Surface.*—Smooth.
- *Thickness.*—Thin.
- *Texture.*—Tough.
- *Color.*—Light green before maturity, turning to Gold Green (14–L–8) at harvest.
- *Dehiscence.*—Opens freely.
- *Splitting.*—Along suture.

Nut:
- *Size.*—Medium to small. Average length—1 1/8". Average width—3/4". Average thickness—5/8".
- *Nuts per ounce on average sample.*—22.
- *Form.*—Length/width—ovate. Width/thickness—medium to flat.
- *Shell.*—Paper; thin; smooth to ragged. Outer shell—bony. Inner shell—soft.
- *Color.*—Medium Tan (12–L–7).
- *Pits.*—Small, numerous; round.
- *Base.*—Ventrally oblique.
- *Stem scar.*—Small.
- *Apex.*—Acute.
- *Wing.*—Narrow; thin.
- *Inner surface.*—Medium.
- *Ventral streak.*—Dark; broad; long; point acute.
- *Percentage of kernel to nut on average sample.*—66 percent.

Kernel:
- *Size.*—Medium to small. Average length—7/8". Average width—7/16". Average thickness—5/16".
- *Kernels per ounce on average sample.*—32.
- *Form.*—Length/width—ovate. Width/thickness—medium to flat.
- *Base.*—Ventrally oblique.
- *Stem scar.*—Small.
- *Apex.*—Obtuse to acute.
- *Surface.*—Smooth.
- *Pellicle.*—Thin.
- *Pubescence.*—Smooth.
- *Color.*—Medium Light Brown (14–L–12).
- *Number of doubles.*—Few.
- *Defective kernels.*—Very few.
- *Flavor.*—Normal.
- *Quality.*—Good.

The tree and its nuts herein described may vary in slight detail due to climatic and soil conditions under which this variety may be grown; the present description being of the variety as grown in the Central Valley of California.

The following is claimed:

A new and distinct variety of almond tree, substantially as illustrated and described, which bears general resemblance to the Nonpareil but is characterized by a tree which is larger, as well as more vigorous and upright in growth; by a blooming period approximately three or four days later and which is about halfway between the Nonpareil and Mission; by intercompatibility with both the Nonpareil and Mission; and by crop production greater than the Nonpareil but with nuts and kernels which, while resembling said Nonpareil, average ten to twenty percent smaller in size.

No references cited.